US011179037B2

(12) United States Patent
Brown et al.

(10) Patent No.: US 11,179,037 B2
(45) Date of Patent: Nov. 23, 2021

(54) PATIENT MONITOR SCREEN AGGREGATION

(71) Applicant: ZOLL Medical Corporation, Chelmsford, MA (US)

(72) Inventors: Eric W. Brown, Saugus, MA (US); Dan M. Mihai, Hanover Park, IL (US); Frederick J. Geheb, Danvers, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

(21) Appl. No.: 16/906,325

(22) Filed: Jun. 19, 2020

(65) Prior Publication Data

US 2020/0383572 A1   Dec. 10, 2020

Related U.S. Application Data

(63) Continuation of application No. 16/404,262, filed on May 6, 2019, now Pat. No. 10,722,119, which is a
(Continued)

(51) Int. Cl.
*A61B 5/00* (2006.01)
*A61N 1/39* (2006.01)
(Continued)

(52) U.S. Cl.
CPC .......... *A61B 5/0022* (2013.01); *A61B 5/0002* (2013.01); *A61B 5/0004* (2013.01);
(Continued)

(58) Field of Classification Search
CPC ........ G16H 40/63; G16H 40/67; G16H 10/60; A61N 1/3993; A61B 34/10; A61B 5/0002; A61B 5/0004; A61B 5/0022
See application file for complete search history.

(56) References Cited

U.S. PATENT DOCUMENTS 5,987,519 A   11/1999  Peifer et al.
6,731,311 B2   5/2004  Bufe et al.
(Continued)

OTHER PUBLICATIONS

U.S. Appl. No. 16/404,262, filed May 6, 2019, Pending.
(Continued)

*Primary Examiner* — Orlando Bousono
(74) *Attorney, Agent, or Firm* — Finch & Maloney PLLC

(57) ABSTRACT

A remote interface system according to some embodiments includes one or more patient monitoring devices having one or more sensors for patient monitoring, one or more first processors to receive information from the sensors and generate patient data based thereon, a web server, a first communication system, and a first screen to display a representation of at least a first portion of the patient data, and a remote interface device including a second communication system, a second screen, one or more second processors, an application executed by the one or more second processors and configured to detect a presence of the first communication system, establish a communication link between the first and second communication systems, establish a reliable connection channel (e.g. secure websocket connection) with the web server, receive the patient data via the connection, and display at least a second portion of the patient data on the second screen.

21 Claims, 7 Drawing Sheets

Related U.S. Application Data continuation of application No. 15/704,841, filed on Sep. 14, 2017, now Pat. No. 10,321,824, which is a continuation of application No. 14/213,662, filed on Mar. 14, 2014, now Pat. No. 9,788,724.

(60) Provisional application No. 61/792,961, filed on Mar. 15, 2013.

(51) Int. Cl.
*A61B 34/10* (2016.01)
*G16H 40/67* (2018.01)

(52) U.S. Cl.
CPC ............ *A61B 34/10* (2016.02); *A61N 1/3993* (2013.01); *G16H 40/67* (2018.01)

(56) References Cited

U.S. PATENT DOCUMENTS

| | | | |
|---|---|---|---|
| 7,027,871 B2 | 4/2006 | Burnes et al. | |
| 8,170,887 B2 | 5/2012 | Rosenfeld et al. | |
| 8,175,895 B2 | 5/2012 | Rosenfeld et al. | |
| 9,788,724 B2 | 10/2017 | Brown et al. | |
| 10,321,824 B2 | 6/2019 | Brown et al. | |
| 2001/0044586 A1 | 11/2001 | Ferek-Petric | |
| 2002/0013613 A1 | 1/2002 | Haller et al. | |
| 2002/0052539 A1 | 5/2002 | Haller et al. | |
| 2002/0082665 A1 | 6/2002 | Haller et al. | |
| 2002/0103508 A1 | 8/2002 | Mathur | |
| 2002/0123673 A1 | 9/2002 | Webb et al. | |
| 2002/0181680 A1 | 12/2002 | Linder et al. | |
| 2002/0193846 A1 | 12/2002 | Pool et al. | |
| 2003/0025602 A1 | 2/2003 | Medema et al. | |
| 2003/0041866 A1 | 3/2003 | Linberg et al. | |
| 2004/0061716 A1 | 4/2004 | Cheung et al. | |
| 2004/0155772 A1 | 8/2004 | Medema et al. | |
| 2005/0159787 A1 | 7/2005 | Linberg et al. | |
| 2005/0203350 A1 | 9/2005 | Beck | |
| 2005/0216311 A1 | 9/2005 | Gmelin et al. | |
| 2006/0161213 A1 | 7/2006 | Patel | |
| 2006/0161214 A1 | 7/2006 | Patel | |
| 2006/0189854 A1 | 8/2006 | Webb et al. | |
| 2006/0287586 A1 | 12/2006 | Murphy | |
| 2007/0271122 A1 | 11/2007 | Zaleski | |
| 2009/0171412 A1 | 7/2009 | Kelly et al. | |
| 2011/0172550 A1 | 7/2011 | Martin et al. | |
| 2011/0227739 A1 | 9/2011 | Gilham et al. | |
| 2011/0246235 A1 | 10/2011 | Powell et al. | |
| 2011/0270631 A1 | 11/2011 | Cambray et al. | |
| 2011/0295078 A1 | 12/2011 | Reid et al. | |
| 2012/0078647 A1 | 3/2012 | Grassle et al. | |
| 2012/0130204 A1 | 5/2012 | Basta et al. | |
| 2012/0179012 A1 | 7/2012 | Saffarian | |
| 2012/0226768 A1* | 9/2012 | Gaines | A61B 5/0026 709/217 |
| 2012/0226771 A1* | 9/2012 | Harrington | G16H 40/67 709/217 |
| 2013/0054467 A1 | 2/2013 | Dala et al. | |
| 2013/0162433 A1 | 6/2013 | Muhsin et al. | |
| 2013/0231711 A1 | 9/2013 | Kaib | |
| 2013/0231947 A1 | 9/2013 | Shusterman | |
| 2013/0254087 A1 | 9/2013 | Rooz et al. | |
| 2013/0267873 A1 | 10/2013 | Fuchs | |
| 2013/0275152 A1 | 10/2013 | Moore et al. | |
| 2014/0018779 A1 | 1/2014 | Worrell et al. | |
| 2014/0019901 A1* | 1/2014 | Powell | G06F 3/0485 715/771 |
| 2014/0122120 A1 | 5/2014 | Doudian | |
| 2014/0235293 A1 | 8/2014 | Sheldon | |
| 2014/0249850 A1* | 9/2014 | Woodson | G16H 20/00 705/3 |
| 2014/0266794 A1 | 9/2014 | Brown et al. | |
| 2015/0019231 A1* | 1/2015 | Sadler | G16H 30/20 705/2 |
| 2018/0092535 A1 | 4/2018 | Brown et al. | |
| 2019/0254521 A1 | 8/2019 | Brown et al. | |

OTHER PUBLICATIONS

U.S. Appl. No. 15/704,841, filed Sep. 14, 2017, Patented.
U.S. Appl. No. 14/213,662, filed Mar. 14, 2014, Patented.
U.S. Appl. No. 61/792,961, U.S. Appl. No. 61/792,962, Expired.
Rescorla, E. "HTTP Over TLS," The Internet Society, Network Working Group. RFC2818, May 2000. 7 pages. *
WebSocket.org, "HTML5 Webs Sockets: A Quantum Leap in Scalability for the Web," dated Mar. 4, 2013, retrieved Nov. 11, 2016. 6 pages. *
WebSocket.org, "About HTML5 WebSockets," dated Mar. 4, 2013, retrieved Nov. 11, 2016. 3 pages. *
Fette, I. "The WebSocket Protocol", Internet Engineering Task Force, RFC6455, Dec. 2011, 7 pages. *
International Search Report and Written Opinion issued in PCT/US2014/028704 dated Aug. 15, 2014, 27 pages. *
SureSigns VMB Portal Bedside Monitor—Essential Measurements for Multiple Care Environments Phillips Medical Systems, 2011. 4 pages. *
SureSigns VSV Vital Signs Viewer—Basic Central Viewing and Alarming Phillips Medical Systems, 2007 4 pages. *

* cited by examiner

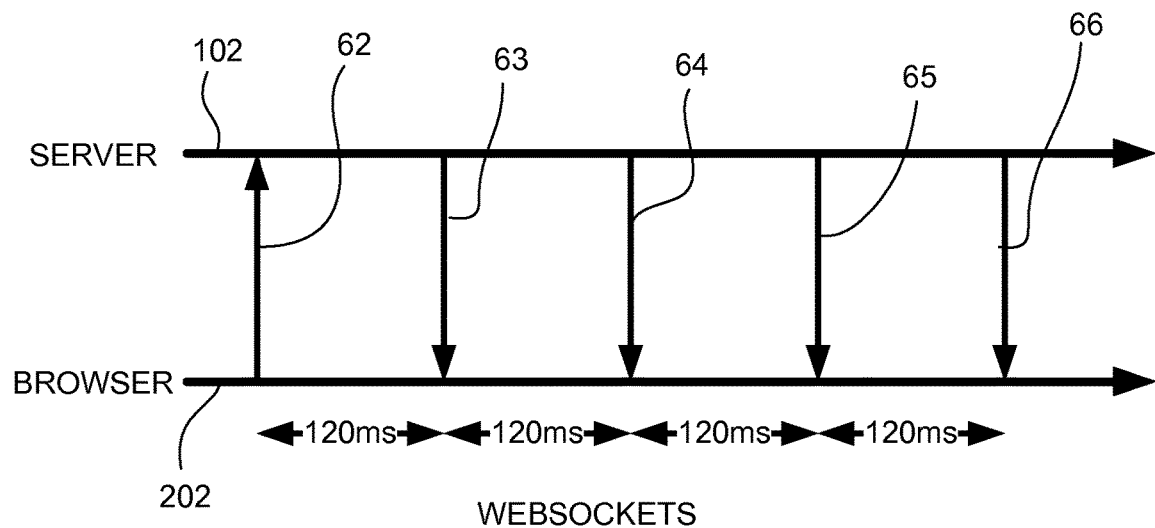
FIG. 6 WEBSOCKETS
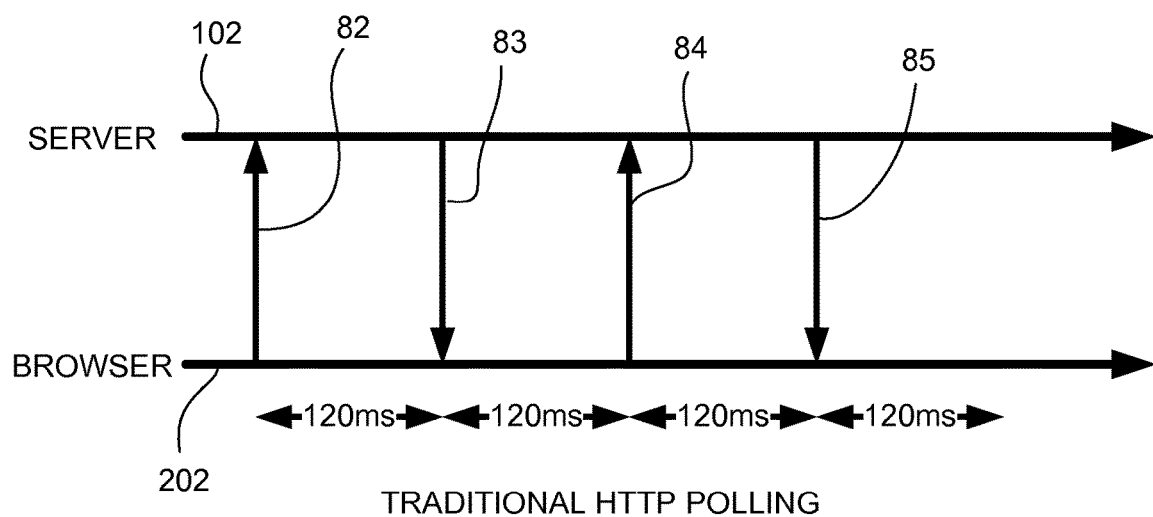
FIG. 8 TRADITIONAL HTTP POLLING

PATIENT MONITOR SCREEN AGGREGATION

CROSS-REFERENCE TO RELATED APPLICATIONS

This application is a continuation of and claims the benefit under 35 U.S.C. § 120 of U.S. patent application Ser. No. 16/404,262, filed on May 6, 2019, entitled "Patient Monitor Screen Aggregation," which claims priority to and the benefit of U.S. Non-Provisional patent application Ser. No. 15/704,841, filed on Sep. 14, 2017, now U.S. Pat. No. 10,321,824, which claims priority to and the benefit of U.S. Non-Provisional patent application Ser. No. 14/213,662, filed on Mar. 14, 2014, now U.S. Pat. No. 9,788,724, which claims priority to and the benefit of U.S. Provisional Patent Application Ser. No. 61/792,961, filed on Mar. 15, 2013. This application is also related to Patent Cooperation Treaty Application No. PCT/US14/28704, filed on Mar. 14, 2014, all of which are incorporated herein by reference in their entireties for all purposes.

TECHNICAL FIELD

Embodiments of the present invention relate to remote screen and data aggregation of information from multiple patient monitoring devices.

BACKGROUND

Patient monitoring devices, for example defibrillators, typically include a user interface screen for displaying data acquired about the patient, for example via sensors in communication with the patient monitoring device and with the patient. Such patient monitoring devices are often portable. Data acquisition from such devices, even streaming data acquisition, can often be delayed or cumbersome due to the large amounts of data collected by the patient monitoring device, and/or the connection limitations of current streaming technologies.

Such conventional streaming technologies typically include a latency of at least one second or more, and/or rely upon a proprietary standard that makes it difficult for other devices to connect to receive data. Systems that permit remote viewing a user interface also often do not permit the user interfaces from multiple devices to be aggregated on a single screen, and also often do not permit display of information from the device other than the information corresponding to that which is simultaneously displayed on the monitoring device.

SUMMARY

In Example 1, a remote interface system for medical application, the remote interface system comprising: a patient monitoring device comprising: one or more sensors configured for physical attachment to a patient; a first processor configured to receive information from the one or more sensors and to generate patient data based on the information; a web server; a first communication system; and a first screen configured to display a representation of at least a first portion of the patient data; and a remote interface device comprising: a second communication system; a second screen; a second processor; an application executed by the second processor, the application configured to detect a presence of the first communication system, establish a communication link between the first and second communication systems, establish a websocket connection with the web server, wherein the websocket connection is secure, receive the patient data via the websocket connection, and display at least a second portion of the patient data on the second screen.

In Example 2, the remote interface system of Example 1, wherein the communication link is a direct communication link that does not travel over any wires outside of the patient monitoring device and the remote interface device.

In Example 3, the remote interface system of any of Examples 1-2, wherein at least a portion of the communication link includes a wired network.

In Example 4, the remote interface system of any of Examples 1-3, wherein the patient monitoring device is portable.

In Example 5, the remote interface system of any of In Examples 1-4, wherein the remote interface device is portable.

In Example 6, the remote interface system of any of Examples 1-5, wherein the application is further configured to receive the patient data via the websocket connection in packets each representing 120 milliseconds of the patient data.

In Example 7, the remote interface system of any of Examples 1-6, wherein the web server sends a new packet of the patient data to the remote interface device at least once every 120 milliseconds.

In Example 8, the remote interface system of any of Examples 1-7, wherein the application is further configured to receive the patient data via the websocket connection in packets each representing between 40 and 200 milliseconds of the patient data.

In Example 9, the remote interface system of any of Examples 1-8, wherein packets of the patient data sent by the web server to the remote interface device include ECG waveform data from the patient.

In Example 10, the remote interface system of any of Examples 1-9, wherein packets of the patient data sent by the web server to the remote interface device are structured according to Javascript Object Notation (JSON) protocol.

In Example 11, the remote interface system of any of Examples 1-10, wherein the remote interface device is configured to show portions of the patient data on the second screen which the patient monitoring device is not configured to show on the first screen.

In Example 12 the remote interface system of any of Examples 1-11, wherein the first portion of the patient data is not the same as the second portion of the patient data, and wherein the remote interface device is configured to show the second portion of the patient data simultaneously with the patient monitoring device showing the first portion of the patient data.

In Example 13, the remote interface system of any of Examples 1-12, wherein the patient monitoring device is a first patient monitoring device, the one or more sensors are a first set of one or more sensors, the patient is a first patient, the processor is a first processor, the information is first information, the patient data is first patient data, the web server is a first web server, the communication link is a first communication link, the websocket connection is a first websocket connection, the remote interface system further comprising a second patient monitoring device comprising: a second set of one or more sensors configured for physical attachment to a second patient; a second processor configured to receive second information from the second set of one or more sensors and to generate second patient data based on the second information; a second web server; a third communication system; and a third screen configured to display a representation of at least a first portion of the second patient data; and wherein the application is further configured to detect a presence of the third communication system, establish a second communication link between the first and third communication systems, establish a second websocket connection with the second web server, wherein the second websocket connection is secure, receive the second patient data via the second websocket connection, and display at least a second portion of the second patient data on the second screen.

In Example 14, the remote interface system of any of Examples 1-13, wherein the application is configured to display the at least the second portion of the second patient data on the second screen simultaneously with displaying the at least the second portion of the first patient data on the second screen.

In Example 15, the remote interface system of any of Examples 1-14, wherein the at least the second portion of the first patient data is displayed in a first data window on the second screen, and wherein the at least the second portion of the second patient data is displayed in a second data window on the second screen, and wherein the application is further configured to permit one or both of the first data window and the second data window to be repositioned on the second screen.

In Example 16, the remote interface system of any of Examples 1-15, wherein the at least the second portion of the first patient data is displayed in a first data window on the second screen, and wherein the at least the second portion of the second patient data is displayed in a second data window on the second screen, and wherein the application is further configured to permit, during use of the remote interface system, reassignment of the first data window to display of the at least the second portion of the second patient data.

In Example 17, the remote interface system of any of Examples 1-16, wherein the application is further configured to permit one or both of the first data window and the second data window to be repositioned on the second screen via a drag-and-drop process.

In Example 18, the remote interface system of any of Examples 1-17, wherein the remote interface device is a first remote interface device, the application is a first application, the communication link is a first communication link, the websocket connection is a first websocket connection, the remote interface system further comprising a second remote interface device, the second remote interface device comprising: a third communication system; a third screen; a third processor; a second application executed by the third processor, the second application configured to detect a presence of the first communication system, establish a second communication link between the first and third communication systems, establish a second websocket connection with the web server, wherein the second websocket connection is secure, receive the patient data via the second websocket connection, and display at least a third portion of the patient data on the third screen.

In Example 19, the remote interface system of any of Examples 1-18, wherein the third portion of the patient data is the same as the second portion of the patient data.

In Example 20, the remote interface system any of Examples 1-19, wherein the second application is further configured to display the at least the third portion of the patient data on the third screen simultaneously with the display of the at least the second portion of the patient data on the second screen.

In Example 21, the remote interface system of any of Examples 1-20, wherein the second portion and the third portion of the patient data are different.

In Example 22, the remote interface system of any of Examples 1-21, wherein the patient monitoring device is a defibrillator.

In Example 23, a method for remote interface with a medical device, the method comprising: monitoring a patient with a patient monitoring device, the patient monitoring device having a web server, a first screen, and one or more sensors attached to the patient; generating patient data based on information received from the one or more sensors; displaying at least a first portion of the patient data on the first screen; establishing a secure websocket connection between the web server and a remote interface device; receiving the patient data from the patient monitoring device with the remote interface device via the secure websocket connection; and displaying at least a second portion of the patient data on a second screen on the remote interface device.

In Example 24, the method of Example 23, wherein the secure websocket connection is completely wireless between the patient monitoring device and the remote interface device.

In Example 25, the method of any of Examples 23-24, wherein the secure websocket connection runs through at least a portion of a wired network.

In Example 26, the method of any of In Example 23-25, wherein the patient monitoring device is portable.

In Example 27, the method of any of Examples 23-26, wherein the remote interface device is portable.

In Example 28, the method of any of Examples 23-27, wherein receiving the patient data further comprises receiving the patient data in packets each representing 120 milliseconds of the patient data.

In Example 29, the method of any of Examples 23-28, wherein receiving the patient data further comprises receiving the patient data in packets each representing between 40 and 200 milliseconds of the patient data.

In Example 30, the method of any of Examples 23-29, wherein packets of the patient data sent by the web server to the remote interface device include ECG waveform data from the patient.

In Example 31, the method of any of Examples 23-30, further comprising formatting the patient data into packets of data before sending the patient data with the web server, and wherein the patient data is formatted into the packets according to Javascript Object Notation (JSON) protocol.

In Example 32, the method of any of Examples 23-31, wherein displaying the at least the second portion of the patient data on the second screen comprises displaying the at least the second portion of the patient data on the second screen simultaneously with the displaying of the at least the first portion of the patient data on the first screen.

In Example 33, the method of any of Examples 23-32, wherein the first portion of the patient data is different from the second portion of the patient data.

In Example 34, the method of any of Examples 23-33, wherein the patient monitoring device is a first patient monitoring device, the web server is a first web server, the one or more sensors is a first set of one or more sensors, the patient data is first patient data, the information is first information, and the secure websocket connection is a first secure websocket connection, the method further comprising: monitoring a second patient with a second patient monitoring device, the second patient monitoring device having a second web server, a third screen, and a second set of one or more sensors attached to the second patient; generating second patient data based on second information received from the second set of one or more sensors; displaying at least a first portion of the second patient data on the third screen; establishing a second secure websocket connection between the web server and the remote interface device; receiving the second patient data from the second patient monitoring device via the second secure websocket connection; and displaying at least a second portion of the second patient data on the second screen on the remote interface device.

In Example 35, the method of any of Examples 23-34, wherein the remote interface device is a first remote interface device, and wherein the secure websocket connection is a first secure websocket connection, the method further comprising: establishing a second secure websocket connection between the web server and a second remote interface device; receiving the patient data from the patient monitoring device with the second remote interface device via the second secure websocket connection; and displaying at least a third portion of the patient data on a third screen of the second remote interface device.

In Example 36, the method of any of Examples 23-35, wherein the second portion of the patient data is the same as the third portion of the patient data.

In Example 37, the method of any of Examples 23-36, wherein the first portion of the patient data is the same as the second portion of the patient data.

In Example 38, the method of any of Examples 23-37, wherein the second portion of the patient data is different from the third portion of the patient data.

In Example 39, a remote interface system for medical application, the remote interface system comprising: a patient monitoring device comprising: one or more sensors configured for physical attachment to a patient; a first processor configured to receive information from the one or more sensors and to generate patient data based on the information; a web server; a first communication system; and a first screen configured to display a representation of at least a first portion of the patient data; and a remote interface device comprising: a second communication system; a second screen; a second processor; an application executed by the second processor, the application configured to detect a presence of the first communication system, establish a communication link between the first and second communication systems, establish a reliable connection channel with the web server, wherein the reliable connection channel is secure, receive the patient data via the reliable connection channel, and display at least a second portion of the patient data on the second screen.

In Example 40, while multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 6 illustrates communication and timing between browser and server, according to embodiments of the present invention.

FIG. 8 illustrates communication and timing between browser and server for a traditional http polling situation.

Figure 1:
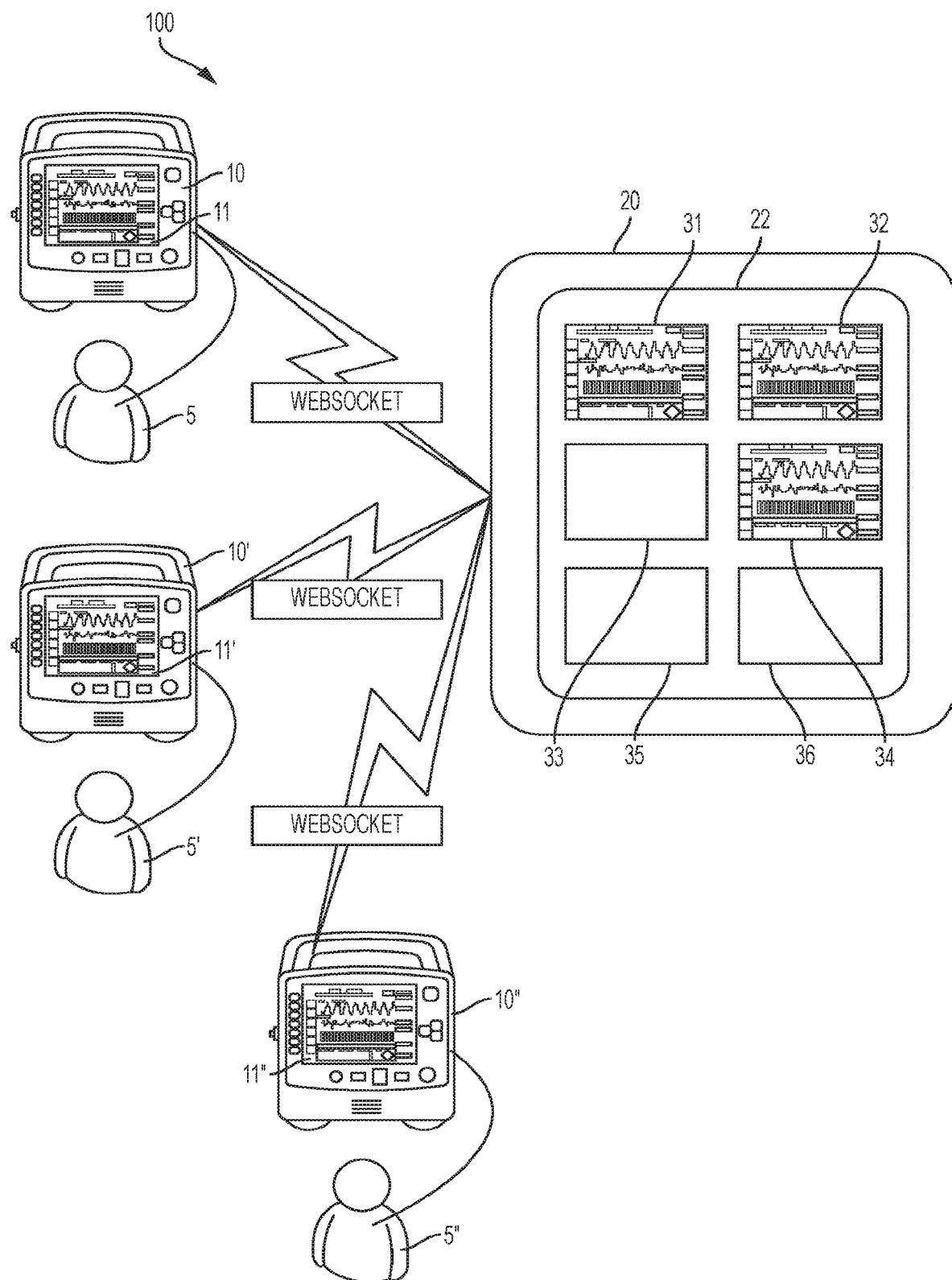
FIG. 1 illustrates a screen aggregation system, according to embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 illustrates a screen aggregation system 100, which may also be referred to as a remote interface system, including patient monitoring devices 10 each configured for physical attachment to patient 5, according to embodiments of the present invention. As one example, patient monitoring device 10 may be a defibrillator, and electrodes from the defibrillator 10 may be attached to the patient 5. For example, device 10 may be a ZOLL® X Series or R Series patient monitor and defibrillator equipped as described herein. Other sensors may also be attached to the patient, either physically or wirelessly, for example a blood pressure sensor, heart rate monitor, or a pulse oximeter. The monitoring device 10 may include a display screen 11 configured to display information about the patient 5, for example the patient's electrocardiogram ECG wave data, blood pressure over time, heart rate, pulse oximetry data, alarms, and other patient information, according to embodiments of the present invention.

FIG. 1 also illustrates a remote interface device 20, which may also be referred to as a screen aggregation device 20, which is configured to communicate wirelessly or with a wired connection with each of the patient monitoring devices 10. The remote interface device 20 includes a screen 22 for displaying information. The screen 22 may be controlled by a display module which causes the screen 22 to display information about two or more of the patient monitoring devices 10. For example, as shown in FIG. 1, the screen 22 may be configured to display the user interface screen 11 of each device 10 in one of six screen positions 31-36 of screen 22. For example, the user interface 11 of one device 10 is shown in screen position 31; the user interface 11' of another device 10' is shown in screen position 32; and the user interface 11" of another device 10" is shown in screen position 34. According to some embodiments, the user interfaces 11, 11', 11" are viewed remotely on screen 22 in "real time," such that what is displayed on each of user interfaces 11, 11', 11" is displayed simultaneously on screen 22.

According to other embodiments of the present invention, the screen 22 is configured to display information or data received from devices 10, 10', 10" other than, and/or in addition to, the information or data simultaneously displayed on screens 11, 11', 11". In some cases, the screen 22 is configured to display information or data from devices 10, 10', 10" which those devices are simply unable to display, or are not configured to display under any circumstances. This could include data which may be deemed not important enough to display on the device 10 due to device's role in monitoring a patient and conveying critical patient information, and may also include data of a different type or format than that displayed on device 10, including for example historical data or combinations or plots of certain data types.

Although six screen positions 31-36 are shown on device 20, one of ordinary skill in the art will appreciate based on the present disclosure that various other numbers, shapes, layouts, and configurations of screen positions may be used, according to embodiments of the present invention.

Figure 2:
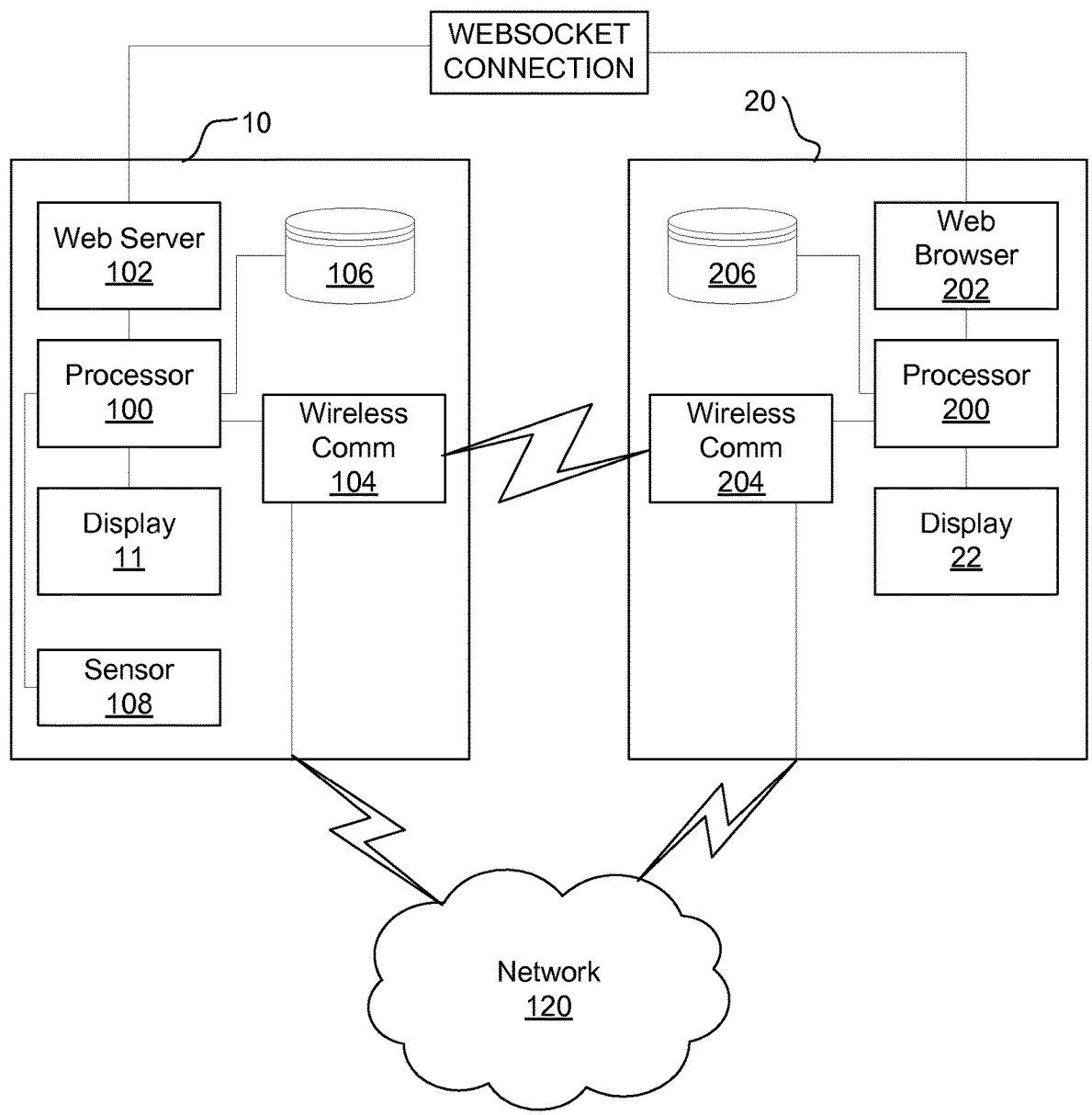
FIG. 2 illustrates a screen aggregation system, according to embodiments of the present invention.

FIG. 2 illustrates a device 10 and device 20, according to embodiments of the present invention. Patient monitoring device 10 may include one or more sensors 108 configured for physical attachment to a patient, a processor 100 configured to receive information from the one or more sensors 108 and to generate patient data based on the information, a web server 102, a wireless or wired communication system 104, a database 106, and a display or screen 11 configured to display a representation of at least a portion of the patient data. The remote interface device 20 includes a wireless or wired communication system 204, a screen or display 22, a processor 200, and a web browser 202, according to embodiments of the present invention. The processor 200 may be configured to run an application, for example in the form of instructions stored in database 206 and executable by processor 200. Such an application may be configured to detect a presence of the first wireless or wired communication system 104. This detection may be accomplished using an auto-discovery system, for example multicast domain name system (mDNS). Example of auto-discovery systems that may be used by processor 200 to discover the communication system 104 include Apple Bonjour and Rendezvous, Avahi, Zeroconf, mDNS, and the like. As used herein, "communication system" is used in its broadest sense to refer to a system capable of establishing communications, either directly or indirectly, and via one or a combination of a wired, wireless, or other connection capable of exchanging information.

Once communication system 104 is discovered (e.g. its presence is discovered within a certain wireless range of device 20), a communication link is established between communication system 104 and communication system 204. This may be a direct wireless connection between wireless communications systems 104, 204, wherein the communication link does not travel over any wires outside of the patient monitoring device 10 and the remote interface device 20. Alternatively, this may be an indirect wireless connection, for example via a wired network 120, according to embodiments of the present invention. Alternatively, this may be a direct wired connection, either direct or via network 120, according to embodiments of the present invention. Next a websocket connection is established between web browser 202 and web server 102. The websocket connection may employ the WebSocket Protocol as defined by the Internet Engineering Task Force (IETF) and WebSocket API as described in publications of the W3C as part of the HTML5 initiative. The websocket connection may alternatively be based on, but not conforming to, such protocols and APIs. The websocket connection may be a reliable connection channel, even if such reliable connection channel is not a WebSocket connection. According to some embodiments of the present invention, the websocket connection is secure and/or encrypted, for example using standard TCP/IP encryption techniques such as basic authentication with secure socket layer (SSL) encryption. Once the websocket connection is established, the processor 200 receives patient data via the websocket connection (via web browser 202), and displays at least a portion of the patient data on the screen 22, according to embodiments of the present invention. According to some embodiments of the present invention, a websocket connection is a low latency bi-directional communication pipe, for example having a latency of 40-200 ms, which, once established, is not driven by requests like HTTP but is instead an established communications pipe.

FIG. 6 illustrates an example of the establishment of a websocket connection between server 102 and browser 202, according to embodiments of the present invention. In server request 62, the browser 202 sends a request to the server 102 to establish a websocket connection, and then the server 102 sends responses 63-66 back to the browser 202. According to some embodiments of the present invention, each server response 63-66 includes 120 milliseconds (ms) of patient data from patient monitoring device 10. For some patient data, this includes an average or other data processing result of sample data taken at a rate of one sample per 4 ms; for other patient data, this includes a new waveform (e.g. ECG waveform) or changes to the waveform (or other plot or graph) over the 120 ms period. As such, because each of the messages 63-66 includes a 120 ms block of data, the websocket messages 63-66 may be sent every 120 ms as shown, according to embodiments of the present invention. These websocket messages significantly reduce latency compared with a streaming data setup, because no additional server request, other than the initializing websocket server request 62, is necessary in order to prompt the sending of messages 63-66 to the browser 202. According to some embodiments of the present invention, each message 63-66 includes 40 to 200 ms of patient data, and each message 63-66 is sent 40-200 ms apart.

The websocket connection of FIG. 6 may be compared with the illustration of a traditional http polling connection of FIG. 8. FIG. 8 illustrates an example of the establishment of a streaming or polling connection between server 102 and browser 202, according to embodiments of the present invention. In server request 82, the browser 202 sends a request for content to the server 102, including full header information, and then the server 102 sends a response 83 back to the browser 202. The browser 202 then sends another request for content 84 to the server 102, and then the server 102 sends the next response 85 back to the browser 202. This continues back-and-forth, thus increasing the overall latency of the connection compared with a websocket connection. In the connection of FIG. 8, a separate request is made for each period of patient data, and each separate request is responded to with the particular requested information. By contrast, with the websocket connection of FIG. 6, once the communication pipe is established, the server 102 continues to send each period of the patient data even without it being further requested, according to embodiments of the present invention.

The websocket messages 63-66 may be sent in the form of packets, for example having a header and a payload (e.g. patient data). The packet may be formatted according to the JavaScript Object Notation (JSON) protocol or other suitable format. Using a protocol such as JSON provides a data format that is relatively easy to parse and interpret, in a non-proprietary sense, which permits designers of screen aggregation devices or other web browser-enabled devices to more easily design an interface with devices 10, according to embodiments of the present invention. As such, in some embodiments the communications connection between devices 10 and 20 may be secure and authenticated, for example using SSL, but the patient data itself may be human-readable and sent via websockets in the JSON or similar protocol. JSON is a text-based format that is language-independent and human-readable. Some elements of the data structure may include values (e.g. a heart rate value), while other elements may include arrays (e.g. data sufficient to reconstruct a patient's ECG waveform over the sample period). JSON also compresses well, and most off-the-shelf web browsers have the ability to handle JSON compression. Objects may be named with strings which help other users identify the data type for such object for use in subsequent parsing, according to embodiments of the present invention. Use of such protocol may also reduce an overall amount of code, by permitting recipients of the patient data to easily parse it rather than interpreting, converting, and/or translating it. The data sent via the websocket connection may be compressed using customary supported compression standards, according to embodiments of the present invention. Other nonproprietary or proprietary data formats or standards may be used for the data transmitted by the websocket connection, according to embodiments of the present invention.

Figure 3:
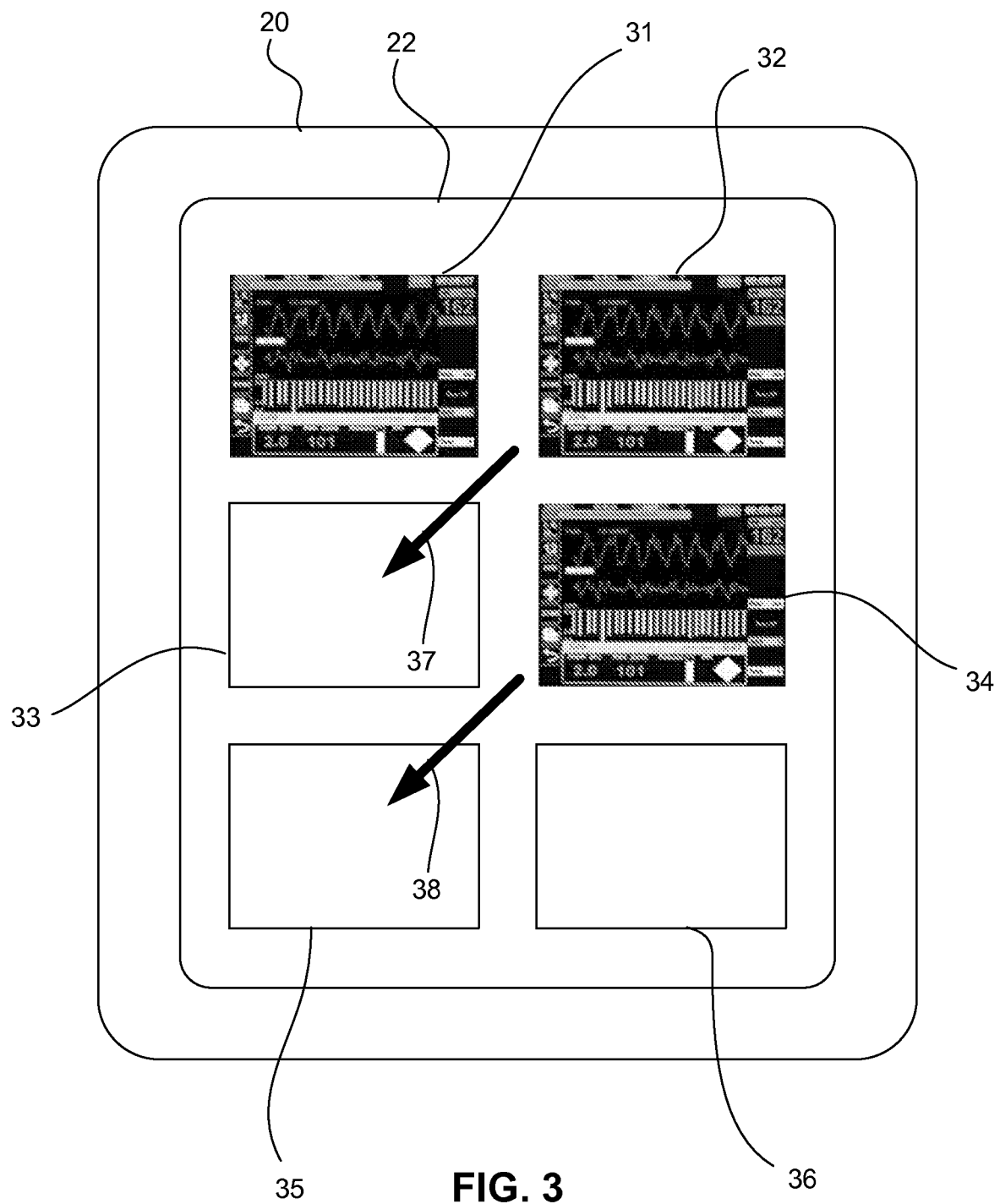
FIG. 3 illustrates a screen aggregation display, according to embodiments of the present invention.
Figure 4:
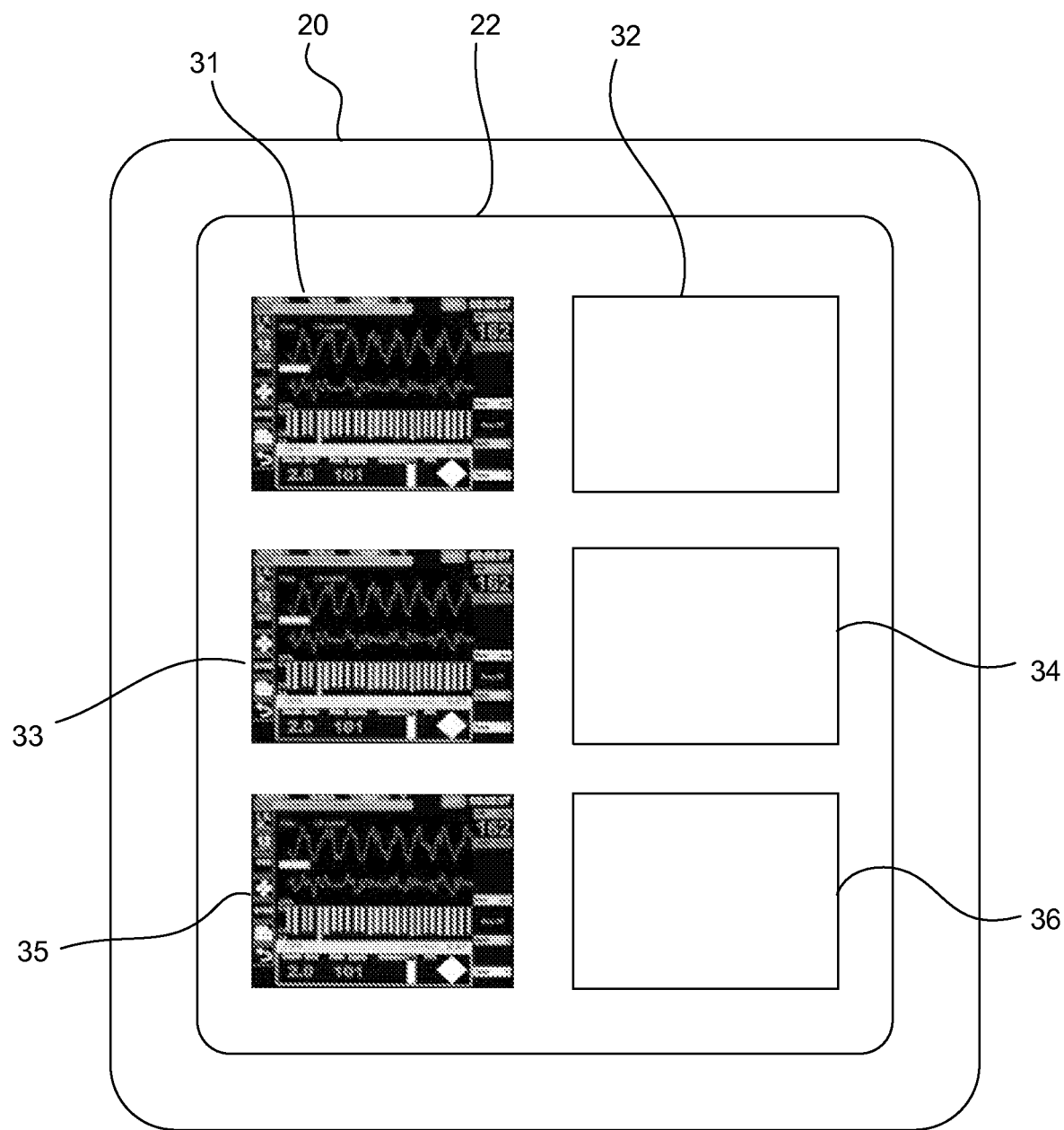
FIG. 4 illustrates the screen aggregation display of FIG. 3 with remote screen displays repositioned.

FIGS. 3 and 4 illustrate example screen displays 22, showing that screen positions for user interface displays may be changed or customized by the user. For example, FIG. 3 shows a simultaneous display of three screens from three different devices 10, 10', 10". The user interface displayed in screen position 32 may be moved to a new screen position 33, for example by selecting the user interface in position 32 and dragging it to screen position 33 in the direction of arrow 37, according to embodiments of the present invention. Similarly, the user interface displayed in screen position 34 may be moved to a new screen position 35, for example by selecting the user interface in position 32 and dragging it to screen position 35 in the direction of arrow 38, according to embodiments of the present invention. This would result in the new screen 22 layout resembling that of FIG. 4. Screen positions 31-36 may alternatively be referred to as "slots."

In addition to moving screen displays to different positions on the aggregated screen 22, new websocket connections may be established between device 20 and other patient monitoring devices. For example, the device aggregation application running on device 20 may permit the user to select a menu or listing of patient monitoring devices 10 that have been discovered or that are available for connection, permitting the user to select one of the devices with which to establish a new websockets connection. According to some embodiments of the present invention, the application may also prompt the user to specify a screen location for the new user interface display on screen 22. According to some embodiments of the present invention, the application permits reconfiguration "on the fly" of which display "slots" or screen positions 31-36 are in communication with which devices 10.

According to embodiments of the present invention, the aggregation device 20 may itself be connected to one or more additional internal or external monitors or screens (not shown), and the user may reassign and/or rearrange the screen position corresponding to each device 10 to which device 20 is connected across any of the "slots" on any of the screens associated with device 20, according to embodiments of the present invention. This ability is dynamic and does not affect the devices 10, 10', 10" to which the device 20 is connected, or the connectivity as between the devices 10, 10', 10" and the aggregation console device 20, according to embodiments of the present invention. In a similar manner, a screen replication, or other data from, the same device 10 may be placed in more than one "slot" simultaneously anywhere among the various "slots" of the device 20 and its associated monitors or screens. The same device 10 interface may also be displayed simultaneously by two or more different aggregation devices 20, according to embodiments of the present invention. This ability is dynamic and does not affect the devices 10, 10', 10" involved, according to embodiments of the present invention.

According to some embodiments of the present invention, the arrangement and number of slots 31-36 on each device 20 and across multiple screens 22 of device 20 is configurable. A default configuration including a particular number of slots may be requested during a request for a particular frame from any one of the devices 10, 10', 10", according to embodiments of the present invention.

FIG. 4 also illustrates an additional visual arrangement which may be used with screen 22 on device 20, according to embodiments of the present invention. Screen positions 31, 33, 35 each replicate a display 11, 11', 11" of one of devices 10, 10', 10" simultaneously with those displays, while screen positions 32, 34, 36 may be used to display information that is in addition to the information currently displayed by the device 10, 10', 10" itself, and may even include information which the respective patient monitoring device is incapable of displaying. For example, screen position 31 may be configured to simultaneously replicate a user interface 11 of device 10, while screen position 32 may be configured to display a different format for the same data as displayed in screen position 31, or data or a portion thereof that is received via the websocket connection with device 10 and that is in addition to or different from the data shown in screen position 31. According to some embodiments of the present invention, screen positions 31 and 32 each display different portions of the patient data received via the same websocket connection; according to other embodiments of the present invention, screen positions 31 and 32 each display patient data or portions of patient data received via independent websocket connections with the same device 10.

The screen aggregation device 20 may be a portable computing device, for example a computing tablet or mobile device, according to embodiments of the present invention. According to some embodiments of the present invention, device 10 may also be configured to generate a portable document format (PDF) report and send it to a subscribing device (e.g. device 20) via a websocket link. The web server 102 may also support regular HTTP requests for data, for example a historical database of patient data stored in database 106, according to embodiments of the present invention. Because device 10 includes a web server 102, the device 20 may be any computing device, for example an off-the-shelf computer with no special software pre-installed. In this scenario, the application which device 20 runs in order to connect with device 10 may be transmitted from the web server 102 to the browser 202 and executed in order to install or open the application on the second device 20. In other words, the web server 102 also permits any special software used to receive the data from device 10 to be sent directly to any other device 20 with a web browser 202 and processor 200, according to embodiments of the present invention.

For example, the device 20 can request both the console frame software (e.g. the software that makes the browser display the one or more slots or screen positions 31-36 on screen 22) and the device content (e.g. device screen content) from any of devices 10, 10', 10" because each of those devices may include servers 102 that are able to provide not only the content but the software for viewing the content. A user of console 20 can make a request (to device 10) for the console frame (e.g. the screen replication of device screen 11) and preselect in the request the number of available slots per monitor or screen for the console 20. Once the frame software is loaded at the console 20, the frame software does not need to be loaded again unless the console's 20 browser 202 stops, according to embodiments of the present invention.

At the screen aggregation console 20, the user may configure the number of slots per monitor or screen, and the arrangement of the slots on each monitor or screen of console 20. This information about the configuration, arrangement, and/or number of slots per monitor or screen can be stored and updated in a configuration file. The configuration file may be stored, for example, on the console device 20, which may in some cases be a PC. Configuration files are compatible with frame software originating from any device, according to embodiments of the present invention. The configuration file may be in a JSON file format, though other file formats or implementations will suitably store the information, according to embodiments of the present invention. Such configuration files may be accessed from cloud storage, and/or carried with or associated with each user, such that the configuration file for a user is useable with frame software originating from any device 10, 10', 10", according to embodiments of the present invention.

According to some embodiments of the present invention, for devices 10 which are temporarily or permanently fixed in location (e.g. in a temporary hospital ward), the screen 22 may include a map of the geographic or physical location, with the screen positions 31 overlaid at a position corresponding to the location of the corresponding device on the map, to permit a person who is viewing aggregated information from one or more devices in the particular ward or location to see where in such ward or location the device is located. According to some embodiments of the present invention, instead of screen positions 31 overlaid on the map, the map includes characters or icons showing a location of a device 10 with an availability for a websocket connection, and a user's selection of such icon or character establishes the websocket connection and/or changes all or a portion of the screen 22 to display the patient data from such websocket connection. According to embodiments of the present invention, the device 20 permits the data shown on screen 22, or portions thereof, to be selected and/or enlarged and/or minimized.

While FIG. 2 shows a single patient monitoring device 10 communicably coupled with a single remote interface system 20, one of ordinary skill in the art will appreciate that remote interface system 20 may be communicably coupled, for example via websocket connections, with multiple patient monitoring devices 10. For example, device 20 may even be coupled with more patient monitoring devices 10 than device 20 is capable of visually representing at any one time on screen 22. In such cases, the screen 22 may permit vertical and/or horizontal scrolling in order to view additional screen positions and additional user interface displays. According to some embodiments, a user may select a particular screen position, for example screen position 31, which causes the user interface screen 11 displayed at that screen position to become enlarged and/or to enlarge to the full size of screen 22.

Additionally, multiple remote interface devices 20 may establish websocket connections with the same patient monitoring device 10. As such, multiple screen aggregators 20 may be used, each with its own or a subset of devices 10, 10', 10" displayed, permitting the user of devices 20 to decide which screens to aggregate on that particular device at a particular time. Such websocket connections would be established as described herein, according to embodiments of the present invention.

While device 10 is described as a patient monitoring device, device 10 may alternatively be a different type of device, for example a different type of medical device 10, which has a visual display. For example, the device 10 may be a navigation device located in an ambulance, and the screen aggregator 20 may be used to simultaneously display the user interface (and/or associated data) from the navigation device alongside the user interface (and/or associated data) from the patient monitoring device 10 for the patient 5 in the same ambulance, according to embodiments of the present invention. Such non-patient monitoring devices may establish websocket connections similarly to those described above for the connections between devices 10 and devices 20, according to embodiments of the present invention.

According to some embodiments of the present invention, for example for web browsers 202 which do not fully support HTML5 functionality, the patient data information may be packaged into a browser cookie, such that it is transmitted to the browser via a browser session, rather than with a basic authentication header. While this workaround achieves increased performance over existing streaming and permits the systems described herein to work with a wider range of browsers, it may exhibit a latency that is larger than that of websockets.

Figure 5:
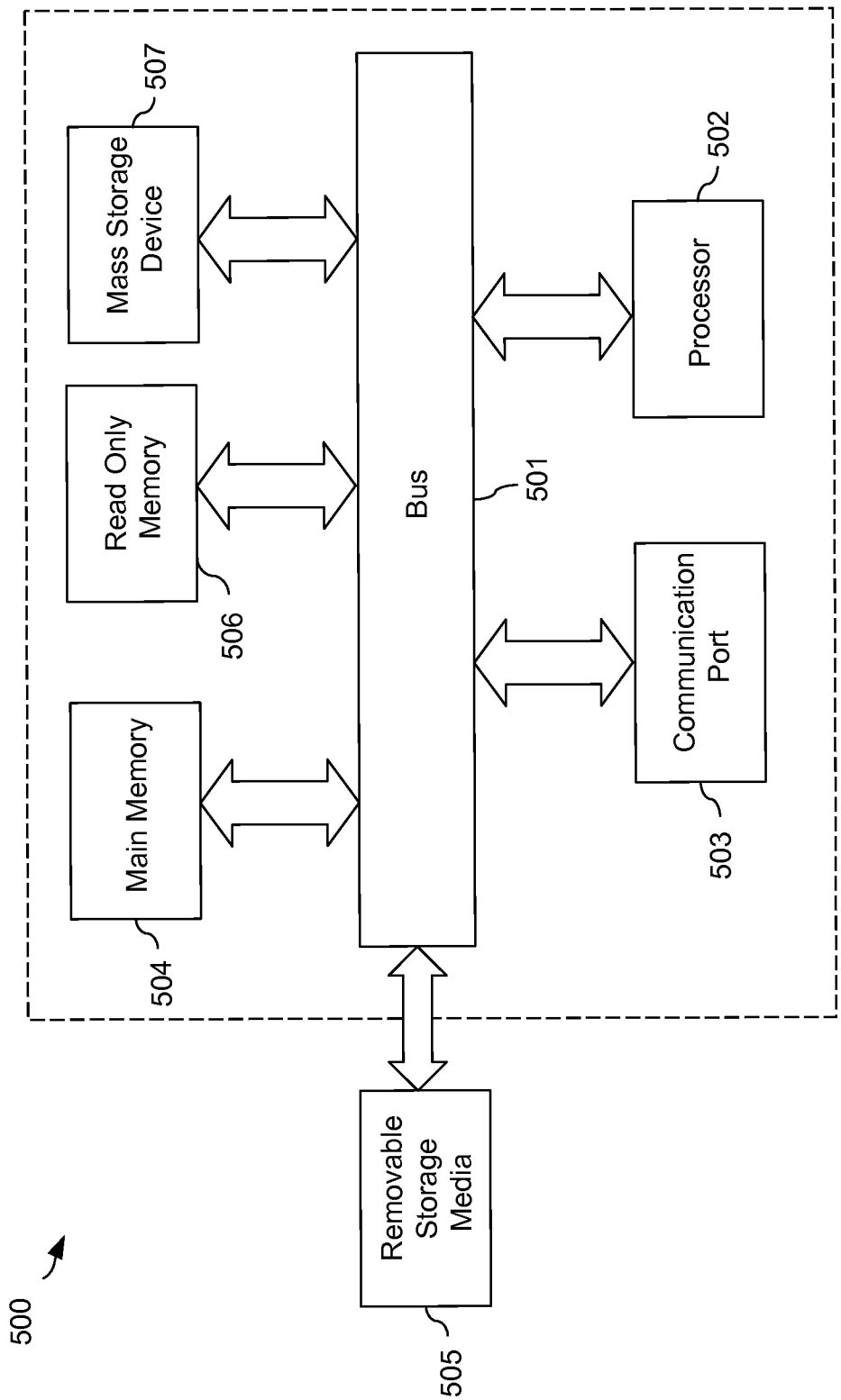
FIG. 5 illustrates a computer system, according to embodiments of the present invention.

FIG. 5 is an example of a computer or computing device system 500 with which embodiments of the present invention may be utilized. For example, devices 10 or 20 may be or incorporate a computer system 500, according to embodiments of the present invention. According to the present example, the computer system includes a bus 501, at least one processor 502, at least one communication port 503, a main memory 504, a removable storage media 505, a read only memory 506, and a mass storage 507.

Processor(s) 502 can be any known processor, such as, but not limited to, an Intel® Itanium® or Itanium 2® processor(s), or AMD® Opteron® or Athlon MP® processor(s), or Motorola® lines of processors, or any known microprocessor or processor for a mobile device, such as, but not limited to, ARM, Intel Pentium Mobile, Intel Core i5 Mobile, AMD A6 Series, AMD Phenom II Quad Core Mobile, or like devices. Communication port(s) 503 can be any of an RS-232 port for use with a modem based dialup connection, a copper or fiber 10/100/1000 Ethernet port, or a Bluetooth® or WiFi interface, for example. Communication port(s) 503 may be chosen depending on a network such a Local Area Network (LAN), Wide Area Network (WAN), Virtual Private Network (VPN) or any network to which the computer system 500 connects. Main memory 504 can be Random Access Memory (RAM), or any other dynamic storage device(s) commonly known to one of ordinary skill in the art. Read only memory 506 can be any static storage device(s) such as Programmable Read Only Memory (PROM) chips for storing static information such as instructions for processor 502, for example.

Mass storage 507 can be used to store information and instructions. For example, flash memory or other storage media may be used, including removable or dedicated memory in a mobile or portable device, according to embodiments of the present invention. As another example, hard disks such as the Adaptec® family of SCSI drives, an optical disc, an array of disks such as RAID (e.g. the Adaptec family of RAID drives), or any other mass storage devices may be used. Bus 501 communicably couples processor(s) 502 with the other memory, storage and communication blocks. Bus 501 can be a PCI/PCI-X or SCSI based system bus depending on the storage devices used, for example. Removable storage media 505 can be any kind of external hard-drives, floppy drives, flash drives, zip drives, compact disc-read only memory (CD-ROM), compact disc-re-writable (CD-RW), or digital video disk-read only memory (DVD-ROM), for example. The components described above are meant to exemplify some types of possibilities. In no way should the aforementioned examples limit the scope of the invention, as they are only exemplary embodiments of computer system 500 and related components.

Figure 7:
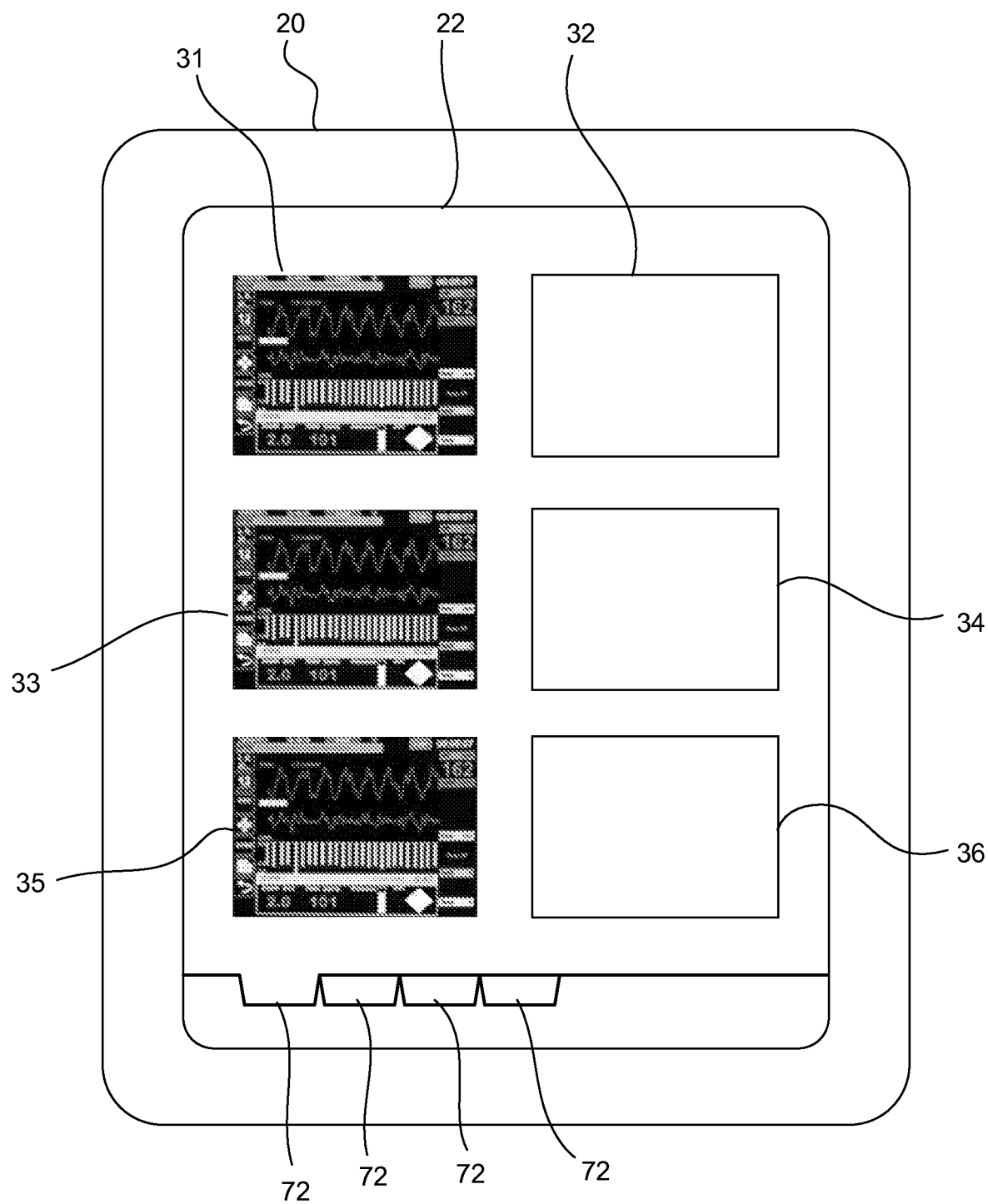
FIG. 7 illustrates an alternative screen aggregation display, according to embodiments of the present invention.

FIG. 7 illustrates an alternative screen aggregation display, according to embodiments of the present invention. The display on the screen of FIG. 7 includes one or more tabs 72 which permit a user to select a "layer" of screens to view at any one time. Each tab 72 may correspond to a screen having its own set of screen positions 31-36, and not all the devices 10 to which device 20 is communicably connected need be displayed simultaneously on the same screen. Also, while device is illustrated in FIGS. 1, 3, 4, and 7 as resembling an interface of a tablet computing device, one of ordinary skill in the art will understand, based on the present disclosure, that other kinds of devices 20 may be employed in a similar fashion, for example desktops, servers, personal computers, "smart" televisions, personal mobile devices, music players, and other devices.

According to some embodiments of the present invention, the aggregation device 20, and/or the software application running on the aggregation device 20 to aggregate and display data from various monitoring devices 10, 10', 10", is configured to emit an audible alarm and/or a visual alarm when any device 10, 10', 10" monitored by the aggregation device 20 issues an alarm. The device 20 or its software may employ a global alarm suspend feature, which permits the alarm caused by any of the devices 10, 10', 10" on device 20 to be suspended for a configurable number of minutes (for example, by permitting the user to select a button or a software button to suspend the alarm). When the configurable number of minutes has passed, and at least one device 10, 10', 10" alarm is still active, the console 20 alarm is reactivated, according to embodiments of the present invention. According to other embodiments of the present invention, the global alarm (i.e. the visual and/or audible alarm on the console device 20) is initiated or resumed if an alarm from a new or additional monitored device 10 is initiated while the global alarm suspend period is still active. In other words, the alarm suspend is interrupted and the sound is reactivated by a new alarm being initiated, either from the same device 10 or a new device 10', 10" from the plurality of devices configured to interact with the aggregation console 20, according to embodiments of the present invention.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A patient monitoring system for medical applications, the patient monitoring system comprising:
an external defibrillator and a mobile device, the external defibrillator comprising:
one or more sensors configured for physical attachment to a patient and to acquire patient data,
a first screen configured to display information about the patient,
a first wireless communication system, and
at least one first processor coupled with the one or more sensors, the first screen, and the first wireless communication system, the at least one first processor configured to:
receive and process the acquired patient data from the one or more sensors,
control the first screen to display at least one first portion of the patient data,
establish a wireless communications connection with the mobile device, and
transmit the patient data to the mobile device via the wireless communications connection; and
the mobile device comprising:
a second screen configured to display information about the patient,
a second wireless communication system, and
at least one second processor coupled with the second screen and the second wireless communication system, the at least one second processor configured to:
establish the wireless communications connection with the external defibrillator,
receive and process the transmitted patient data via the wireless communications connection, and
control the second screen to display at least one first portion of the transmitted patient data corresponding to the at least one first portion of the patient data and to display, in response to an input received by a user of the mobile device, at least one second portion of the transmitted patient data different from the at least one first portion of the transmitted patient data.

2. The patient monitoring system of claim 1, wherein the patient data comprises patient electrocardiogram (ECG) data.

3. The patient monitoring system of claim 1, wherein the patient data comprises one or more of blood pressure data, heart rate data, or pulse oximetry data.

4. The patient monitoring system of claim 1, wherein the at least one second processor is configured to control the second screen to replicate the display on the first screen.

5. The patient monitoring system of claim 1, wherein the at least one second portion of the transmitted patient data includes different patient data than the at least one first portion of the transmitted patient data.

6. The patient monitoring system of claim 1, wherein the at least one second portion of the transmitted patient data includes additional patient data compared to the at least one first portion of the transmitted patient data.

7. The patient monitoring system of claim 1, wherein the wireless communications connection is configured to be encrypted using secure socket layer (SSL) encryption.

8. The patient monitoring system of claim 1, wherein the wireless communications connection is configured to provide full-duplex communication between the external defibrillator and the mobile device.

9. The patient monitoring system of claim 1, wherein the at least one second processor is further configured to:
display a row of tabs on the second screen; and control the second screen to display the at least one second portion of the transmitted patient data in response to a selection of a first tab of the row of tabs.

10. The patient monitoring system of claim 9, wherein the at least one second processor is configured to control the second screen to display the at least one first portion of the transmitted patient data in response to a selection of a second tab of the row of tabs, the second tab being different than the first tab.

11. The patient monitoring system of claim 1, wherein the transmitted patient data is first transmitted patient data, and the system further comprising a second external defibrillator comprising:
   one or more second sensors configured for physical attachment to a second patient and to acquire second patient data;
   a third screen configured to display information about the second patient;
   a third wireless communication system; and
   at least one third processor coupled with the one or more second sensors, the third screen, and the third wireless communication system, the at least one third processor configured to:
      receive and process the acquired second patient data from the one or more second sensors,
      control the third screen to display at least one first portion of the second patient data,
      establish a second wireless communications connection with the mobile device, and
      transmit the second patient data to the mobile device via the second wireless communications connection.

12. The patient monitoring system of claim 11, wherein the at least one second processor is further configured to:
   establish the second wireless communications connection with the second external defibrillator;
   receive and process the transmitted second patient data via the second wireless communications connection; and
   control the second screen to display the at least one first portion of the transmitted second patient data and to display, in response to an input received by a user of the mobile device, at least one second portion of the transmitted second patient data different from the at least one first portion of the transmitted second patient data.

13. The patient monitoring system of claim 12, wherein the at least one second processor is configured to control the second screen to replicate the display on the third screen.

14. The patient monitoring system of claim 12, wherein the at least one second processor is further configured to: display a row of tabs on the second screen; and
control the second screen to display the at least one second portion of the transmitted second patient data in response to a selection of a first tab of the row of tabs.

15. The patient monitoring system of claim 14, wherein the at least one second processor is configured to control the second screen to display the at least one first portion of the transmitted second patient data in response to a selection of a second tab of the row of tabs, the second tab being different than the first tab.

16. The patient monitoring system of claim 15, wherein the at least one second processor is configured to control the second screen to display the at least one first portion of the first transmitted patient data in response to a selection of a third tab of the row of tabs, the third tab being different than the first tab and the second tab.

17. The patient monitoring system of claim 16, wherein the at least one second processor is configured to control the second screen to display the at least one second portion of the first transmitted patient data in response to a selection of a fourth tab of the row of tabs, the fourth tab being different than the first tab, second tab, and third tab.

18. The patient monitoring system of claim 14, the at least one second processor is further configured to:
   control the second screen to display both the at least one first portion of the second transmitted patient data and the at least one second portion of the second transmitted patient data in response to a selection of a first tab of the row of tabs; and
   control the second screen to display both the at least one first portion of the first transmitted patient data and the at least one second portion of the first transmitted patient data in response to a selection of a second tab of the row of tabs, the second tab being different than the first tab.

19. The patient monitoring system of claim 1, wherein the at least one second processor is further configured to issue one or both of an audible or visual alarm in response to an alarm being issued by the external defibrillator.

20. The patient monitoring system of claim 19, wherein the at least one second processor is further configured to receive an alarm suspend command and to suspend the alarm being issued by the external defibrillator in response to receiving the alarm suspend command.

21. The patient monitoring system of claim 20, wherein the at least one second processor is further configured to receive a configurable period of time for which to suspend the alarm being issued by the external defibrillator.

* * * * *